United States Patent
Tamarindo

(10) Patent No.: US 10,245,336 B2
(45) Date of Patent: Apr. 2, 2019

(54) SYSTEM FOR HANDLING STERILISATION OF THIN-BODY FLEXIBLE CONTAINERS (POUCH)

(71) Applicant: GUALA PACK S.p.A., Castellazzo Bormida (IT)

(72) Inventor: Stefano Tamarindo, Castellazzo Bormida (IT)

(73) Assignee: Guala Pack S.P.A. (IT)

( * ) Notice: Subject to any disclaimer, the term of this patent is extended or adjusted under 35 U.S.C. 154(b) by 409 days.

(21) Appl. No.: 15/082,969

(22) Filed: Mar. 28, 2016

(65) Prior Publication Data

US 2017/0001743 A1     Jan. 5, 2017

(30) Foreign Application Priority Data

Jul. 1, 2015   (IT) .................. 102015000029638

(51) Int. Cl.

| B65B 55/08 | (2006.01) |
|---|---|
| A61L 2/08 | (2006.01) |
| B65B 43/12 | (2006.01) |
| B65B 5/06 | (2006.01) |
| B65B 5/10 | (2006.01) |
| B65B 7/02 | (2006.01) |
| B65B 61/20 | (2006.01) |
| B67C 7/00 | (2006.01) |

(52) U.S. Cl.
CPC ............... *A61L 2/087* (2013.01); *B65B 5/06* (2013.01); *B65B 5/10* (2013.01); *B65B 7/02* (2013.01); *B65B 43/123* (2013.01); *B65B 55/08* (2013.01); *B65B 61/20* (2013.01); *B67C 7/008* (2013.01); *A61L 2202/11* (2013.01); *A61L 2202/23* (2013.01)

(58) Field of Classification Search
CPC ....................................................... A61L 2/087
See application file for complete search history.

(56) References Cited

U.S. PATENT DOCUMENTS

| 2004/0060261 A1* | 4/2004 | Py ............................. A61L 2/08 53/425 |
|---|---|---|
| 2004/0241041 A1* | 12/2004 | Woodworth .......... A61J 1/1406 422/22 |
| 2014/0215969 A1* | 8/2014 | Parthun ................... A61L 2/087 53/425 |
| 2015/0059288 A1* | 3/2015 | Wu ....................... B65B 55/027 53/426 |

(Continued)

FOREIGN PATENT DOCUMENTS

| EP | 0694477 | 1/1996 |
|---|---|---|
| JP | 2001122225 | 5/2001 |

(Continued)

*Primary Examiner* — J C Jacyna
(74) *Attorney, Agent, or Firm* — Waller Lansden Dortch & Davis, LLP; Matthew C. Cox

(57) ABSTRACT

A system for handling the sterilization of thin-body, pouch-type, flexible containers (1), provides for applying sacrificial closures (200) to the pouches, loading the provisional closed pouches to be sterilized on a transport device (300) for collective transport, to performing the sterilization of the transport device (300) carrying the provisional closed pouches and, finally, separating, in a sterile chamber, the sacrificial closures (200) from the pouches, performing filling and applying an inviolable cap (100).

1 Claim, 5 Drawing Sheets

(56) References Cited

U.S. PATENT DOCUMENTS

| | | | |
|---|---|---|---|
| 2015/0224247 A1* | 8/2015 | McDorman | A61M 5/003 206/569 |
| 2017/0107008 A1* | 4/2017 | Ichikawa | B65B 3/04 |
| 2017/0240334 A1* | 8/2017 | Myerscough | B65D 77/062 |

FOREIGN PATENT DOCUMENTS

| | | |
|---|---|---|
| JP | 2002321715 | 11/2002 |
| JP | 2003237742 | 8/2003 |
| JP | 2014172620 | 9/2014 |
| JP | 2016008055 | 1/2016 |
| WO | WO2012028980 | 3/2012 |
| WO | WO2012055459 | 5/2012 |
| WO | 2014171814 A1 | 10/2014 |
| WO | WO2014171814 | 10/2014 |
| WO | WO2014171834 | 10/2014 |
| WO | WO2016189754 | 12/2016 |

* cited by examiner

SYSTEM FOR HANDLING STERILISATION OF THIN-BODY FLEXIBLE CONTAINERS (POUCH)

CROSS-REFERENCE TO RELATED APPLICATIONS

This application claims priority to foreign patent application IT102015000029638, filed Jul. 1, 2015, which is hereby incorporated by reference in its entirety.

FIELD OF THE INVENTION

This invention relates to a method and an apparatus for the preparation for sterilisation of thin-body flexible containers (generally known as "pouches"). These containers are typically used to contain food products such as fruit juices, yoghurt, fruit or vegetable purée, creams, honey and the like, or medicines, and the like.

BACKGROUND OF THE INVENTION

In the food industry, the sterilisation of this type of container has enormous importance for the prevention of infections and the correct preservation of the food contained in it.

Sometimes, a chemical sterilisation is performed, during which the container is washed with disinfectants, for example hydrogen peroxide, and then dried, before being sent to subsequent filling.

However, chemical sterilisation has some disadvantages such as, for example, the presence of disinfectant residues in the dry container or the presence of areas not disinfected due to complex geometries or irregularities of the container. This disadvantage is particularly felt precisely in the pouch industry.

While, sterilisation by ionising radiation, such as gamma rays or electron beams, is very widespread. For example, the Applicant is the holder of patents EP 2701751 and EP 2701979, relating to electron-beam sterilisation systems.

Usually, sterilisation using ionising radiation is carried out in specialised centres, to which the producer subject of the containers sends them to be treated; after sterilisation, sterile containers are sent to the company who fills and closes them, using techniques that allow maintaining sterile conditions inside the container. These logistics obviously imply considerable transport costs between the sites and a significant management complexity of the containers within the sites themselves.

The purpose of this invention is to provide a method and an apparatus for the preparation for sterilisation of flexible containers, which are able to reduce the impact of such costs, allowing for the management of a high number of containers simultaneously.

This purpose is achieved by the methods, assemblies and transport devices according to the following claims.

BRIEF DESCRIPTION OF THE DRAWINGS

The characteristics and advantages of this invention will be apparent from the following description, given by way of non-limiting example, in accordance with the accompanying figures, in which.

DETAILED DESCRIPTION

Figure 1:
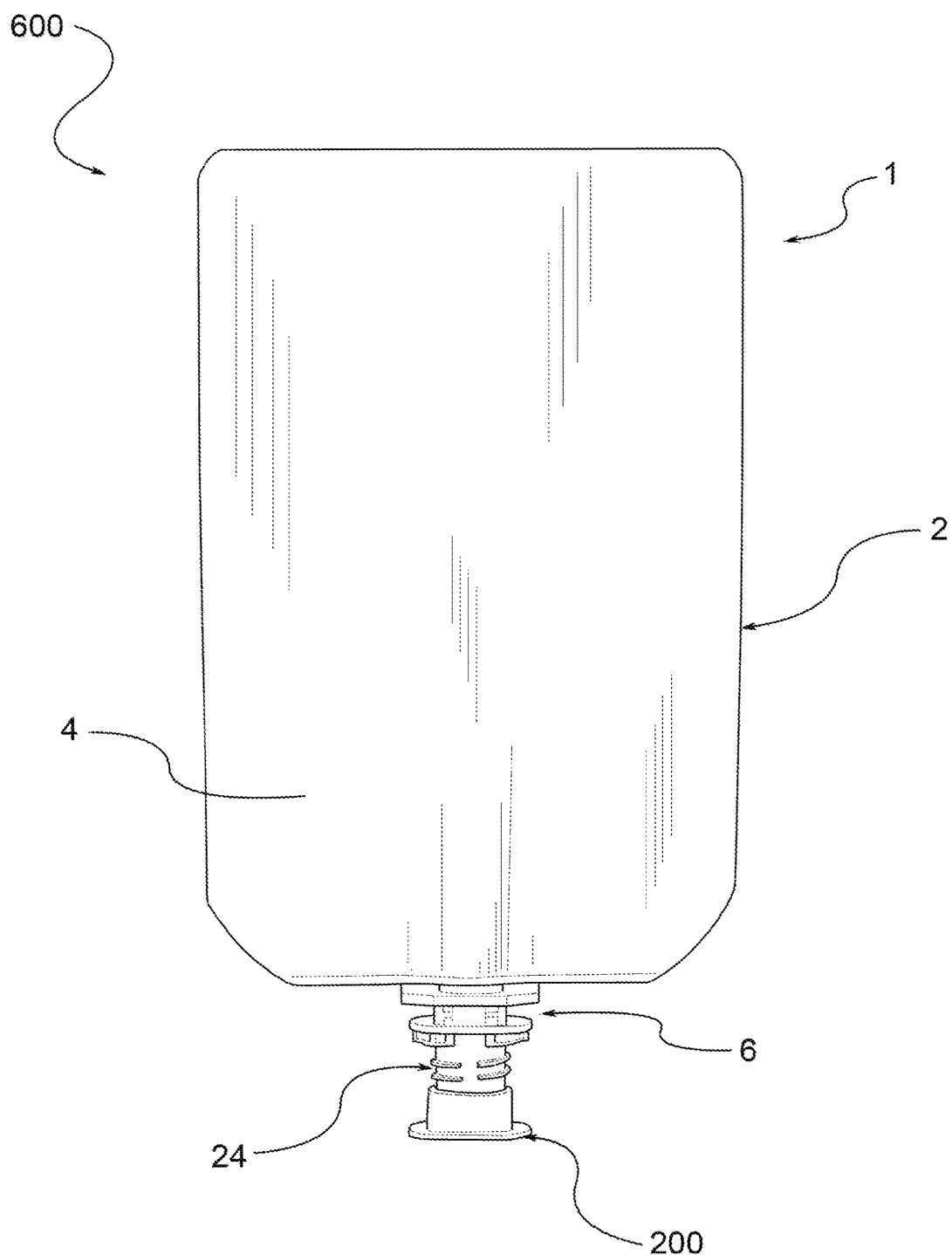
FIG. 1 shows a flexible, thin-body, pouch-type container provided with a sacrificial closure.

With reference to the attached drawings, reference number 1 indicates a flexible, thin-body, pouch-type container as a whole.

The pouch 1 comprises a container body 2 formed by two or more walls 4 consisting of flexible film, facing each other and joined, for example welded, along the edges, possibly with folding lateral walls (gussets) or with a bottom wall.

According to an embodiment, the film is a single layer. Preferably, the film is multilayer.

Preferably, one or ore layers of the film are made from polymers, such as polyolefins, polyamides, polyesters, polycarbonates, polymers derived from renewable sources (bio-based), bio-degradable and compostable.

Preferably, also, one or more layers are coated with metal oxides, for example aluminium oxides, silicon or combinations thereof, or with lacquers, with or without the presence of metal oxides, such as aluminium oxides.

Preferably, also, one or more layers are impermeable to oxygen, moisture and/or light.

Preferably, also, the film is suitable to withstand sterilisation treatments using ionising radiation, as well as some heat treatments such as pasteurisation, freezing, or treatments under pressure or under vacuum.

Preferably, also, the films or individual layers have a thickness between a few nanometers and a few millimeters.

The pouch 1 further comprises a spout 6 made of rigid material, sealingly applied to the body 2. In particular, the spout 6 is typically inserted into a portion of the edge of the body 2, usually between the lateral walls 4.

Preferably, the spout 6 is made, in a single piece, of plastic, for example polyethylene or polypropylene, by injection moulding.

The spout 6 extends substantially along a longitudinal axis Z and comprises, from the part that remains inside the container body 2 of the pouch 1 towards the outside, an entrance portion 8, an intermediate portion 10 and a final portion 12.

Internally, the spout 6 comprises a conduit 14, usually of a circular cylindrical shape, that extends along the longitudinal axis Z, between an inlet 16 of the entrance portion 8 and an outlet mouth 18 of the final portion 12.

The entrance portion 8 is preferably formed by a pair of facing walls 20, with prevailing extension in the transverse direction, i.e., perpendicular to the longitudinal axis Z, joined at the ends. These walls form two outwardly engaging surfaces 22 intended for coupling with the films of the container body 2, preferably by means of welding.

The final portion 12 comprises a tube 24, which extends along the longitudinal axis Z, coaxial with the conduit 14, typically terminating with the outlet mouth 18.

According to an embodiment, the final portion 12 further comprises a threading 26 for screwing a cap 100, realised, for example, by sections of interrupted threading.

Preferably, the cap 100 for the spout 6 comprises an outer annular wall 102, which surrounds the tube 24 and, for example, is provided with threading for engagement with the threading 26 of the spout 6.

At one end of the outer annular wall 102, the cap 100 further comprises a bottom 104 suitable to close the outlet mouth 18 and, at the other end, a tamper-evident seal 106.

Preferably, the final portion 12 of the spout 106 comprises an engaging portion suitable to engage with the tamper-evident seal 106 of the cap 100, to realise an anti-rotation constraint of said tamper-evident seal.

In other words, the cap 100 is applicable to the spout 6 in an inviolable manner, since the unscrewing of the cap causes the tearing of the tamper-evident seal 106, which engages with the engaging portion 6 of the spout.

Furthermore, according to the invention, there is provided a sacrificial closure 200 suitable to be applied to the spout 6, and in particular to the tube 24 of the final portion 12, to close the outlet mouth 18, in a reversible manner.

For example, the sacrificial closure 200 comprises a lateral annular wall 202 that, applied to the closure to the spout 6, extends along the longitudinal axis Z, and a bottom 204, for example made in one piece with the lateral wall 202, for the closure of the outlet mouth 18.

The sacrificial closure 200 is sealingly applicable to the tube 24 of the spout 6, so as to preserve any pre-existing conditions of sterility inside the pouch.

In addition, the sacrificial closure 200 is reversibly applicable to the tube 24 of the spout 6, i.e., in such a way that it is separable from the spout without tears or breaks.

For example, the sacrificial closure 6 is pressure-applicable to the tube 24 of the spout 6, for example in such a way that the lateral wall 202 surrounds the wall of the tube 24 and sealingly engages with it.

The intermediate portion 10 comprises a first support surface 30 and a second support surface 32, lying substantially on planes orthogonal to the longitudinal axis Z and spaced axially.

For example, said support surfaces are constituted by the facing surfaces of a first plate 30a and a second plate 32a, respectively, spaced axially.

Preferably, the first plate 30a is joined to the walls 20 of the entrance portion 8, while the second plate 32a is joined to the engaging portion of the final portion 12.

Preferably, moreover, the intermediate portion 10 has a first guide surface 34 and a second guide surface 36, mutually parallel, parallel to the longitudinal axis Z and equally spaced from this, contained between the support surfaces 30,32.

For example, said guide surfaces are constituted by the facing surfaces of guide walls 34a,36a respectively, spaced transversely.

According to the invention, there is also provided a transport device 300 suitable for loading a plurality of pouches 1 provided with the respective sacrificial closure 200.

Said transport device 300 has a compartment 302 in which, when the pouch with the closure is loaded, at least a portion of the spout 6 and the respective sacrificial closure 200 applied to the spout is received, while any remaining part of the spout 6 and the container body 2 are arranged outside the compartment 302.

Figure 2:
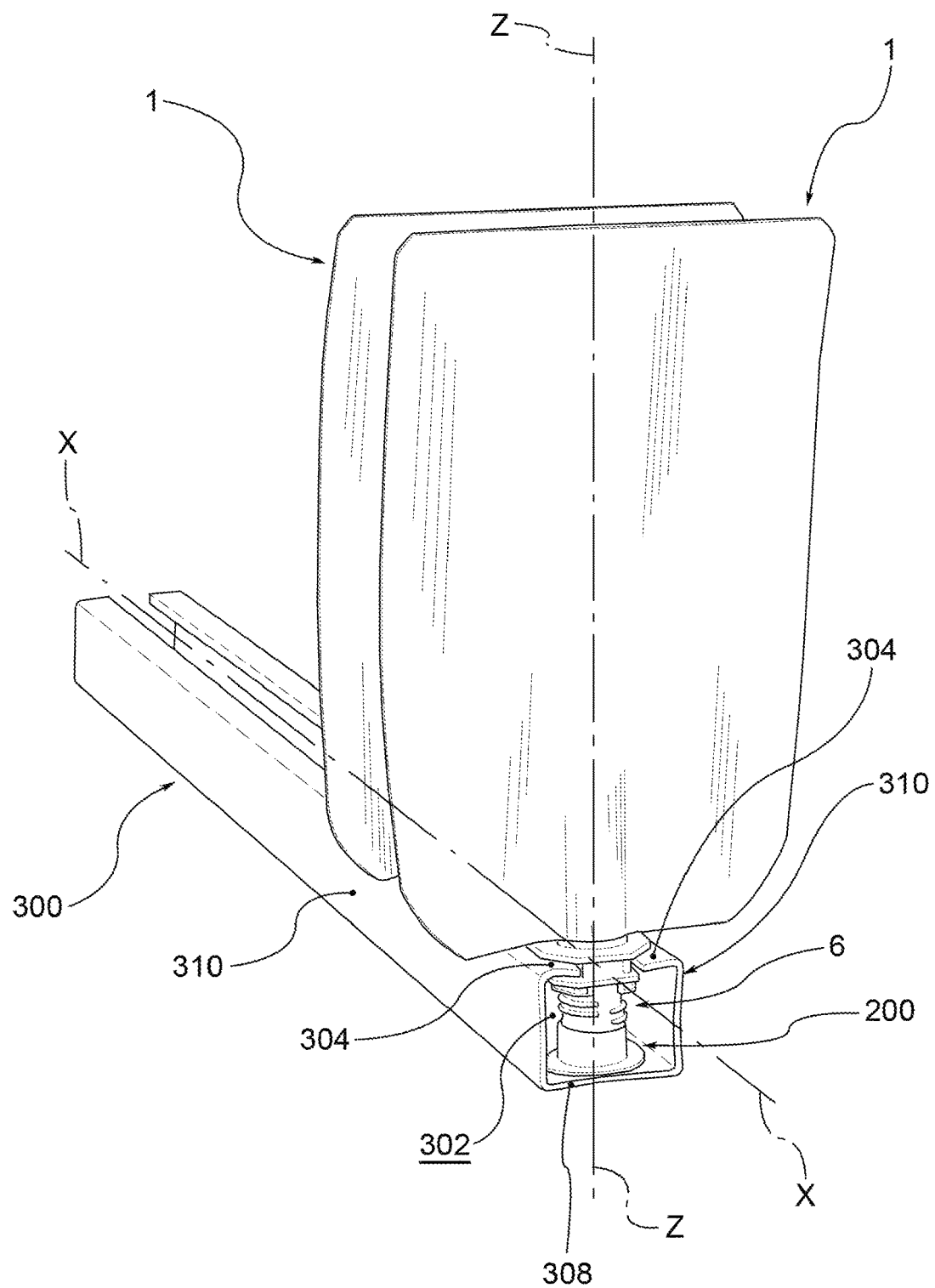
FIG. 2 illustrates a plurality of containers of FIG. 1, loaded on a transport device.
Figure 3:
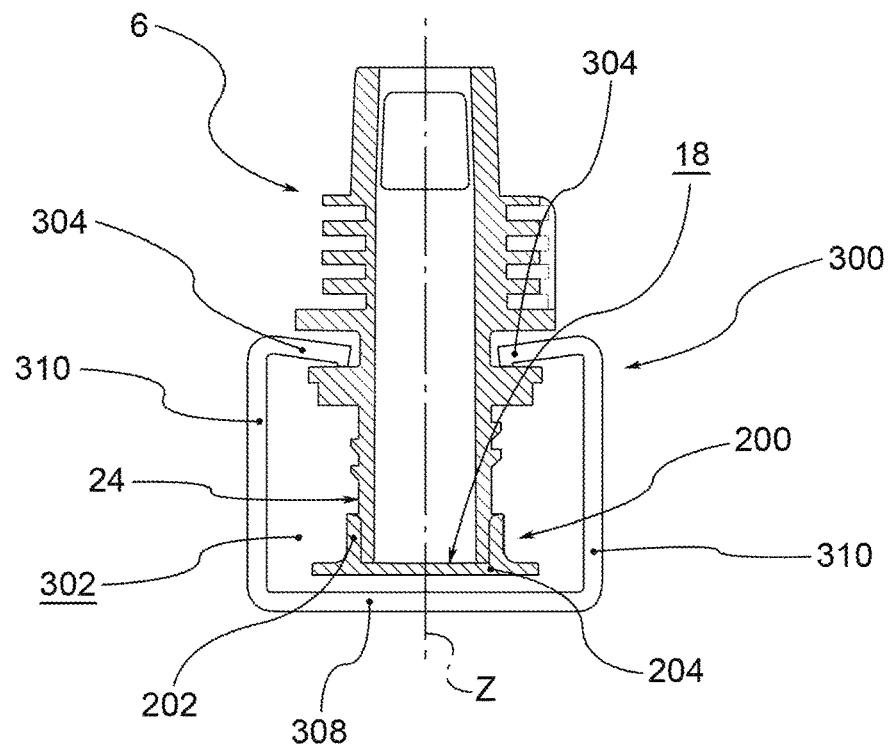
FIG. 3 is a sectional view of a drinking spout provided with the sacrificial closure, partially housed in the transport device, realised according to a first sectional plane, orthogonal to an axis X in FIG. 2.
Figure 4:
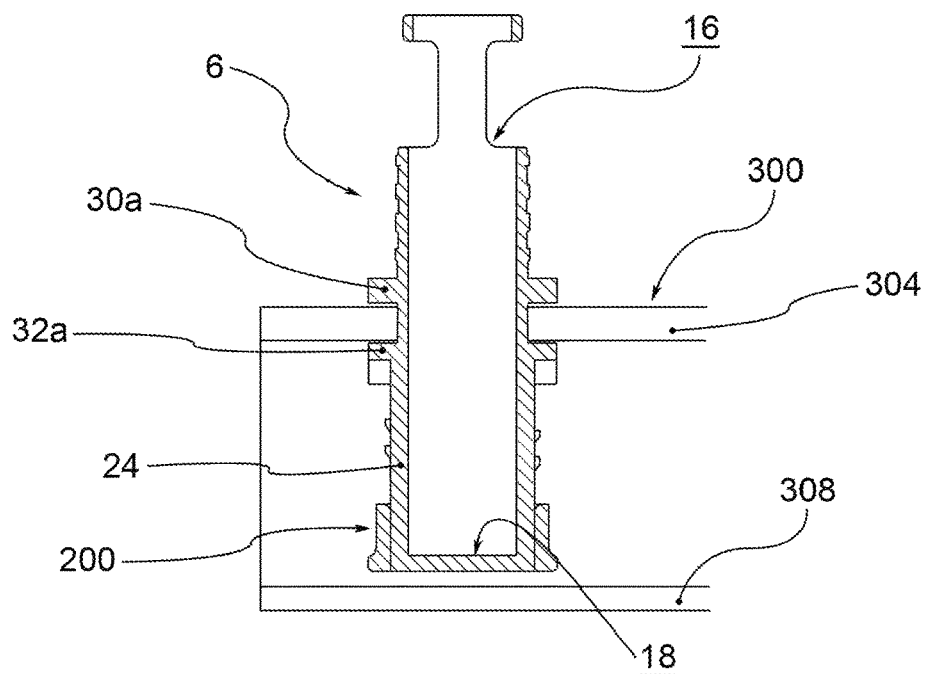
FIG. 4 is a sectional view of the drinking spout provided with the sacrificial closure, partially housed in the transport device, realised according to a first sectional plane, containing the axis X in FIG. 2 and orthogonal to the first sectional plane.
Figure 5:
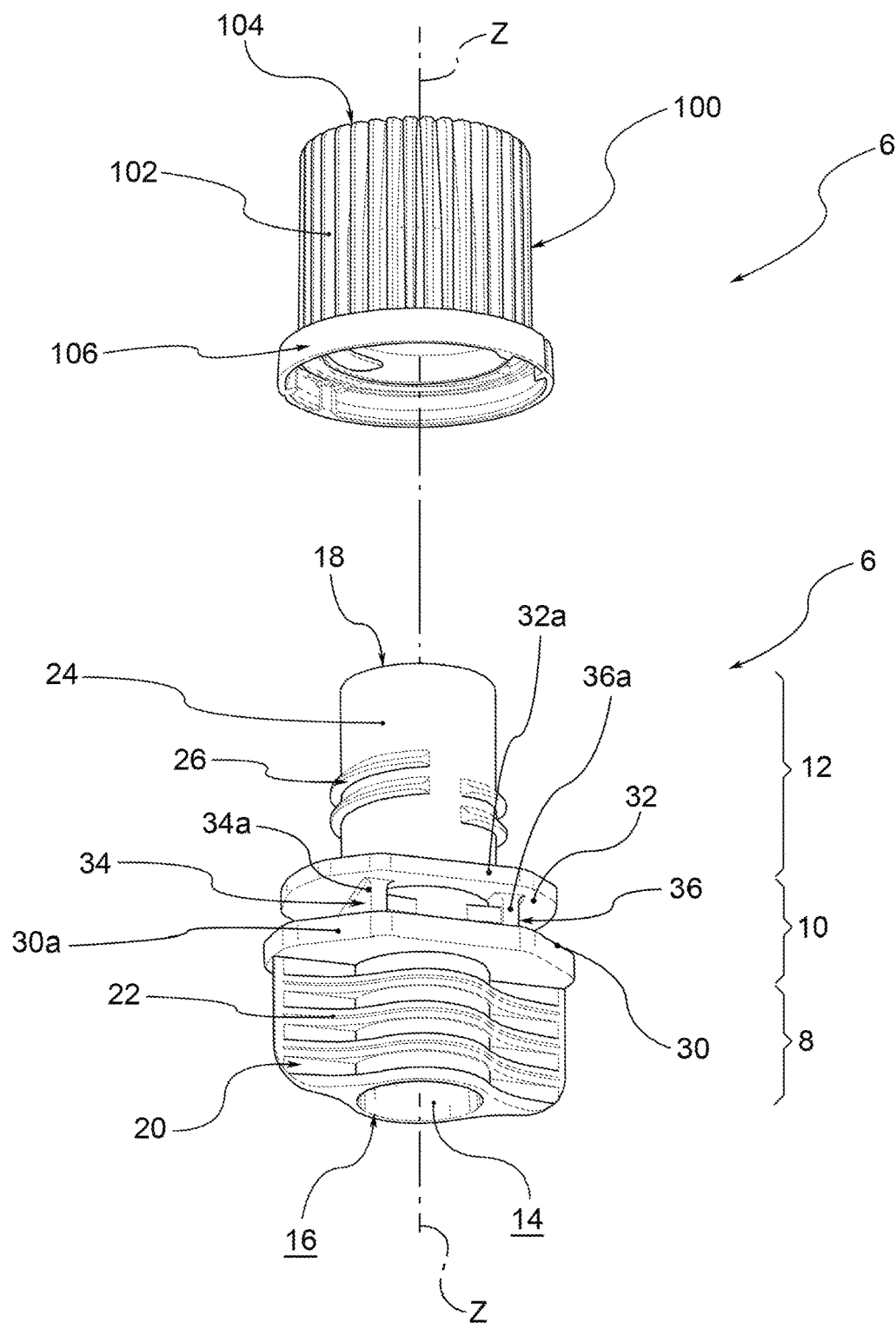
FIG. 5 shows a spout and a final cap applicable to the spout, in separate parts.

In addition, the transport device 300 has support means suitable for engaging the spout 6 and supporting the pouch provided with the closure, both in the "standing" configuration, in which the spout is arranged above and the pouch below, and the "upside down" configuration, in which the spout is arranged below and the pouch above (FIG. 2).

Preferably, said support means comprise a pair of fins 304 suitable to be received between the support surfaces 30,32 of the spout 6, creating a bilateral engagement in the direction of the longitudinal axis Z.

In addition, said engagement means of the transport device 300 are suitable to slidingly engage the spout 6 along a sliding axis X, lying on a plane orthogonal to the longitudinal axis Z.

In particular, said fins 304 allow the pouch to slide with the closure along the sliding axis X; preferably, said sliding is guided by the guide surfaces 34,36 that cooperate with the fins 304.

According to a preferred embodiment, said transport device 300 comprises a section bar having extension along said sliding axis X.

Preferably, said section bar comprises a base 308, flanked by lateral walls 310, surmounted by said fins 304, each projecting from the respective lateral wall 310. The base 308, the lateral walls 310 and the fins 304 peripherally define the compartment 302.

For example, after the pouch 1 with spout 6 is loaded on the section bar, the fins 304 are inserted between the support surfaces 30,32, while the second plate 32a, the tube 24 and the closure 200 are contained in the compartment 302.

According to the invention, a preparation method for sterilisation comprises a first step that involves the production of a plurality of container bodies 2, the production of a plurality of spouts 6 and the production (or reuse) of a plurality of sacrificial closures 200.

The spout 6 is sealingly applied to the respective container body 2, obtaining a plurality of pouches 1. The sacrificial closure 200 is applied, for example by pressure, to the tube 24, realising a provisional closed pouch to be sterilised 600.

In addition, the preparation method for sterilisation comprises a subsequent step of loading a plurality of transport devices 300 with provisional closed pouches to be sterilised, each transport device being loaded with a predetermined number of provisional closed pouches to be sterilised, for collective transport to a sterilising subject.

For example, the loading step involves the insertion by sliding of the provisional closed pouches 600 in said section bar along said sliding axis X and the support of the provisional closed pouch, in the "standing" or "upside down" configuration through the use of the fins 304 between the support surfaces 30,32 of the spouts 6.

Subsequently, preferably, the method involves forming a transport group 400, containing a plurality of transport devices 300, each carrying the closed pouches to be sterilised, stacked.

Figure 6:
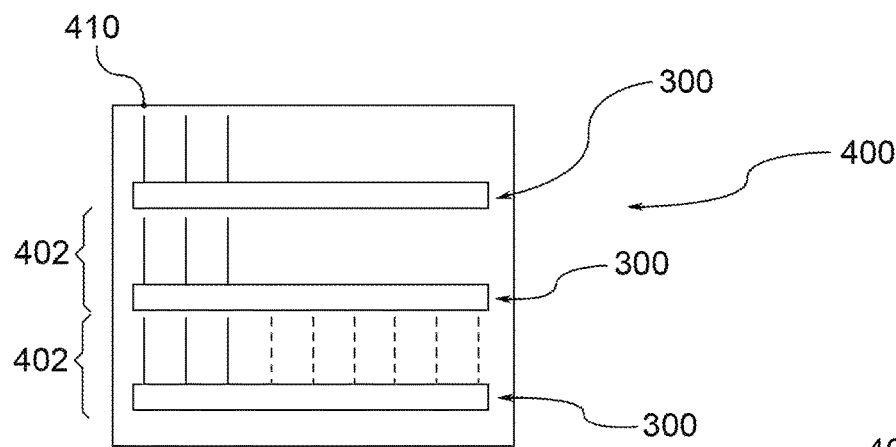
FIGS. 6 and 7 illustrate diagrams of construction variants of transport groups.

According to an embodiment (FIG. 6), the group 400 comprises a plurality of simple transport surfaces 402, wherein each transport surface 402 comprises a predefined number of transport devices 300 placed side by side at the same height, all carrying the provisional pouches arranged in the same direction, for example all "standing" or all "upside down". The transport surfaces 402 are stacked on each other, forming the transport group 400.

Figure 7:
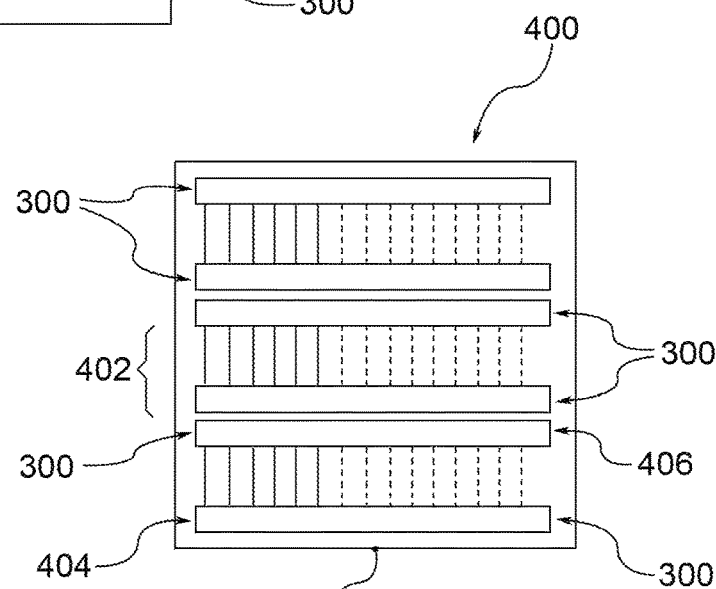
Figure 8:
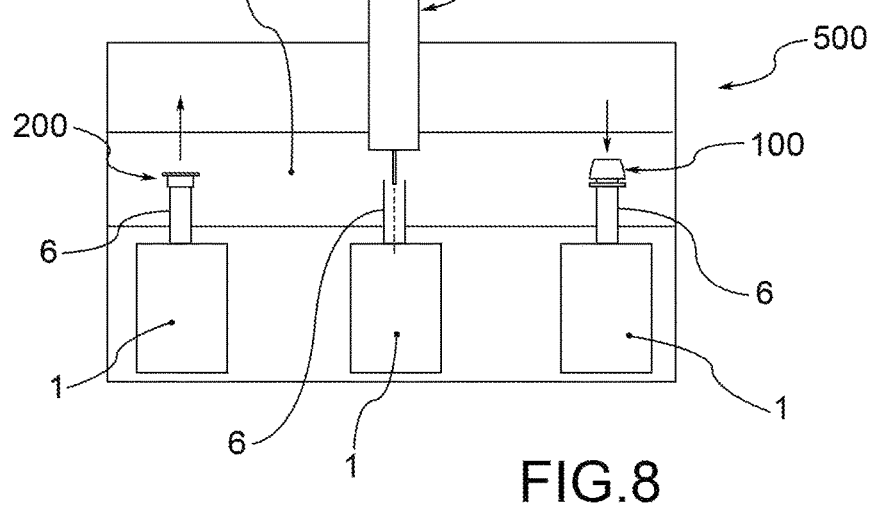
FIG. 8 is a diagram of a filling machine.

According to a further embodiment (FIG. 7), the group 400 comprises a plurality of dual transport surfaces 402, wherein each transport surface comprises a first level 404 comprising a predefined number of transport devices 300 placed side by side at the same height, all carrying the provisional pouches arranged in the same direction, for example all "standing" or all "upside down", and a second level 406 superimposed on the first, comprising a predefined number of transport devices 300 placed side by side and all carrying the provisional pouches arranged in the direction opposite to that of the first level 404, for example all "upside down" or all "standing".

In the transportation surfaces according to this embodiment, the provisional "standing" pouches thus alternate with provisional "upside down" pouches along the sliding axis X.

Even said transport surfaces 402 are stacked on each other, forming the transport group 400.

The loading operations for the formation of the dual transport surfaces are illustrated, for pouches not provided with sacrificial closure, in European patent EP-B1-2611704 in the Applicant's name, whose teachings in this connection are incorporated here.

Generally, the transport group 400 is accommodated in a box 410, for example made of cardboard, for transport.

The method also provides for a possible transport step in which the transport group 400 is transported from the site of the producer subject to a steriliser subject, for example a specialised centre, or a filler subject that also performs sterilisation, where a sterilisation step is performed.

During the sterilisation step, entire transport group 400, whether or not provided with the box 410, or the individual transport surfaces 402 of this, simple or dual, is subjected to sterilisation by ionising radiation.

If the sterilisation step took place in a specialised centre, the transport group 400, constituted by sterilised provisional closed pouches, is transport to the filler subject.

At the subject filler, the sterilised provisional closed pouches are picked from the transport group 400 and sent to a filling machine 500 provided with a sterile chamber 502 suitable to contain, for each sterilised provisional closed pouch, at least a portion of the tube 24 of the spout 6 and the sacrificial closing 200 applied to it.

In the sterile chamber 502 of the machine 500, there is a step of separation of the sacrificial closure 200 from the tube 24, so as to free the access to the outlet mouth 18 of the spout 6.

The sacrificial 200 closures are collected and set aside, and possibly sent for recycling.

The filling machine 500 further comprises filling means 504 that open into the sterile chamber 502, suitable for supplying on command the product to be filled in the pouch 1 through the spout 6. Therefore, there is a filling step.

Finally, in the sterile chamber 502 of the machine 500, there is a step of applying the inviolable cap 100 to the tube 24 of the spout 6.

The final closed pouches thus obtained, still sterile, provided with the cap 100 exit from the sterile chamber 502 and are sent to the subsequent packaging and shipping operations.

Innovatively, the sterilisation management system according to this invention overcomes the drawbacks of the known art, since it allows transporting or handling a large number of pouches, maintaining sterile conditions up to the application of the final cap.

It is clear that one skilled in the art, in order to meet contingent needs, may make changes to the method and device described above, all contained within the scope of protection defined by the claims.

The invention claimed is:

1. Method of sterilisation of flexible pouches, comprising the steps of:
    producing a plurality of pouches, wherein each pouch comprises a container body formed by walls made of flexible film and a spout comprising an entrance portion with an inlet and a tube with an outlet, said spout being sealingly applied to the container body so as to protrude outside of it with at least a section of the tube;
    providing a plurality of sacrificial closures reversibly applicable to the outlet mouth of the spout;
    applying, sealingly and reversibly, the sacrificial closure to the outlet of the spout, thereby obtaining provisionally closed non-filled pouches to be sterilised;
    loading a plurality of provisionally closed non-filled pouches to be sterilised on a transport device for collective transport;
    forming a transport group, containing a plurality of transport devices, each carrying the provisionally closed non-filled pouches to be sterilised, stacked;
    transporting the transport group from the site of the producer subject to a steriliser subject;
    performing a sterlisation of the entire transport group loaded with provisionally closed non-filled pouches, by ionising radiation;
    picking the sterilised provisionally closed non-filled pouches from the transport device and sending them in succession to a sterile chamber;
    for each sterilised provisionally closed non-filled pouch, making at least a portion of the tube provided with the sacrificial closure to pass through the sterile chamber;
    during said passing through of the sterile chamber, separating the sacrificial closure from the tube, filling the sterilised open pouch and applying a tamper-proof cap to the tube to close the pouch.

* * * * *